(12) United States Patent
Ferren (10) Patent No.: US 11,602,268 B2
(45) Date of Patent: Mar. 14, 2023

(54) LARYNGOSCOPE

(71) Applicant: Tracy Don Ferren, Lenexa, KS (US)

(72) Inventor: Tracy Don Ferren, Lenexa, KS (US)

( * ) Notice: Subject to any disclaimer, the term of this patent is extended or adjusted under 35 U.S.C. 154(b) by 134 days.

(21) Appl. No.: 16/106,203

(22) Filed: Aug. 21, 2018

(65) Prior Publication Data
US 2020/0060538 A1   Feb. 27, 2020

(51) Int. Cl.
*A61B 1/267* (2006.01)
*A61B 1/00* (2006.01)

(52) U.S. Cl.
CPC .......... *A61B 1/267* (2013.01); *A61B 1/00071* (2013.01)

(58) Field of Classification Search
CPC ....... A61B 1/267; A61B 1/00052; A61B 1/04; A61B 1/00066; A61B 1/00105; A61B 1/06; A61B 1/2673; A61B 13/00; A61B 1/00071
USPC .................................................. 600/184–199
See application file for complete search history.

(56) References Cited

U.S. PATENT DOCUMENTS

| | | | |
|---|---|---|---|
| 1,396,933 A | 11/1921 | Jacoby | |
| 2,723,661 A | 11/1955 | Hull | |
| 4,112,933 A * | 9/1978 | Moses | A61B 1/267 600/190 |
| 4,611,579 A | 9/1986 | Bellhouse | |
| 4,834,077 A | 5/1989 | Sun | |
| 4,947,896 A | 8/1990 | Bartlett | |
| 5,518,503 A | 5/1996 | Rooney et al. | |
| 5,938,591 A | 8/1999 | Minson | |
| 5,984,863 A | 11/1999 | Ansari | |
| 6,045,499 A | 4/2000 | Pitesky | |
| 6,095,972 A | 8/2000 | Sakamoto | |
| 6,217,514 B1 | 4/2001 | Gruen et al. | |
| 6,231,505 B1 | 5/2001 | Martin | |
| 6,626,829 B1 | 9/2003 | Skaggs | |
| 7,044,910 B2 | 5/2006 | Cartledge et al. | |
| 7,500,948 B2 | 3/2009 | Cantrell | |
| 7,695,433 B2 | 4/2010 | Simons | |
| 7,909,757 B2 | 3/2011 | Herman | |
| 7,955,256 B2 | 6/2011 | Sakamoto | |
| 8,740,788 B1 | 6/2014 | Mettler, Jr. | |
| 9,271,710 B2 | 3/2016 | Grey et al. | |

(Continued)

FOREIGN PATENT DOCUMENTS

EP          0494840          7/1992

*Primary Examiner* — Eduardo C Robert
*Assistant Examiner* — Tara Rose E Carter
(74) *Attorney, Agent, or Firm* — TaeRa Franklin; Eckert Seamans Cherin & Mellott, LLC (57) ABSTRACT

In one embodiment, the present invention relates to a laryngoscope. The laryngoscope includes a blade. The blade includes a first end and a second end extending along the longitudinal axis of the blade. The blade further includes a first edge defining a first side of the blade, as well as a second edge defining a second side of the blade, and the first edge and the second edge extend along a longitudinal axis of the blade. The blade further includes a first curvature from the first end to the second end extending upward along a vertical axis, and a second curvature from the first edge to the second edge also extending upward along the vertical axis. The second curvature allows for considerable tongue control without the need for a large flange that typically causes significant risk of damage to a patient's teeth and other sensitive surrounding tissue.

17 Claims, 7 Drawing Sheets

(56) References Cited

U.S. PATENT DOCUMENTS

| | | |
|---|---|---|
| 9,486,596 B2 | 11/2016 | Qiu |
| 2005/0240081 A1 | 10/2005 | Eliachar |
| 2007/0129607 A1 | 6/2007 | Ashfaque |
| 2010/0198017 A1* | 8/2010 | Raspallo ................ A61B 1/267 |
| | | 600/190 |
| 2011/0092774 A1 | 4/2011 | Herman |
| 2013/0178714 A1 | 7/2013 | Martin |
| 2014/0228645 A1 | 8/2014 | Pourshams |
| 2014/0296645 A1 | 10/2014 | McGrath et al. |
| 2017/0049980 A1 | 2/2017 | Qiu |

* cited by examiner

LARYNGOSCOPE

INTRODUCTION

The present invention relates to devices known as laryngoscopes that are used to facilitate endotracheal intubation of a patient. Specifically, improved laryngoscopes having relatively thin, narrow, and concave surfaces that efficiently control a patient's tongue and epiglottis are described herein.

BACKGROUND

For close to a century, laryngoscopes have been used by medical practitioners as aides in anesthesiology and, in particular, to guide practitioners in the inspection of a patient's throat, as well as the placement of devices therein. Specifically, laryngoscopes typically include a handle and a blade connected to the handle. The blades include a flange extending substantially perpendicular to the blade's longitudinal axis, and is used to control the patient's tongue during the insertion of the laryngoscope into the patient's throat. The blade is then used to displace the patient's epiglottis for better visualization of the larynx. The flange also acts to assist the insertion of, for example, endotracheal tubes into the patient's throat during surgical procedures.

Often times, this flange would cause several drawbacks. Most notably, the flange would cause damage to a patient's teeth during use. Oftentimes, in order to displace the patient's tongue and epiglottis, practitioners unintentionally use the patient's teeth as a fulcrum as they push the patient's tongue and epiglottis into various positions, i.e., "rocking the blade." This in turn often results in damage to the patient's teeth.

Various devices and methods in the art have been developed in an attempt to alleviate this problem. U.S. Patent Application Publication No. 2014/0228645 ("Pourshams"), attempted to alleviate this problem by including protective, elastomeric material to the blade, particularly the surfaces of the flange, in order to minimize the damage caused by interaction between the flange and the teeth. However, this does not resolve the problem, because Pourshams simply accepts the fact that "rocking the blade" is a common technique, and does not attempt to prevent this technique or otherwise limit the interaction between the flange and the teeth. Pourshams is therefore an inefficient attempts to resolve this problem, because direct interaction between the flange and the teeth invariably leads to increased risk of damage to the teeth.

U.S. Pat. No. 7,044,910 ("Cartledge") discloses a removable protective insert that is shaped similar to conventional laryngoscope blades, in that it includes a flange. The protective insert is located in the area of the flange and is designed to reduce pressure on the teeth during intubation. However, like Pourshams, Cartledge continues to employ a flange that directly exposes the teeth to the blade, thereby exposing the teeth to greater than necessary risk of damage from the blade.

U.S. Pat. No. 7,909,757 and U.S. Patent Application Publication No. 2011/0092774 (collectively "Herman") disclose a laryngoscope having a blade with a downwardly convex shape having a pair of flanges extending from the sides of a central axis point. The problems with Herman, however, is that it is a massive structure, only suited for an average-sized to large woman or a small to large man, and not suitable for, for instance, children. Further, the convex structure of Herman tends to simply fill the patient's entire inferior portion of the mouth, moving all other tissue to the outer edges of the patient's mouth so that the practitioner can view the trachea and intubate the patient (see FIG. 15 of Herman). The problem with this, however, is that such a "blunt instrument" approach tends to damage surrounding tissue, and would primarily be of use during extreme emergencies where damage to surrounding tissue is less of a concern than the likelihood that the patient will suffer unnecessary brain damage from lack of oxygen.

U.S. Pat. No. 6,626,829 ("Skaggs") discloses a laryngoscope having a coated blade that provides cushion intended to reduce the possibility of damage to a patient's teeth during intubation. However, much like Pourshams and Cartledge, Skaggs continues the use of a flange, and the direct contact between the flange and the patient's teeth invariably increases the risk of damage caused by the flange, as well as damage to other sensitive areas of the patient's mouth.

There is, therefore, a need for an improved laryngoscope that adequately allows a medical practitioner to control a patient's tongue during use, while also avoiding contact with the patient's teeth, and is capable of performing all of the other necessary functions of a laryngoscope.

SUMMARY OF THE INVENTION

For the purposes of clarity, the term "top portion" is used to describe the dorsal surface of an article. The term "bottom portion" is used to describe the ventral portion of an article.

The term "longitudinal axis" is used to refer to a plane having the greatest length between the outer extremes of an article, which, for example and as will be described in further detail below, may reach from the tip of a laryngoscope to the outer edges of a connecting element.

The terms "transverse axis" or "lateral axis" are used to refer to a plane that depicts a cross section of an article described in the preceding paragraph.

The term "vertical axis" is used to refer to a plane that is perpendicular to the planes described in the preceding two paragraphs.

In various embodiments, a device is disclosed. The device may include a substantially elongate blade; a first end and a second end running along a longitudinal axis of the blade; a first edge and a second edge running along a transverse axis of the blade such that the first edge and the second edge define a width of the blade; a first curvature running from the first edge to the second edge such that the blade further includes a concave first surface defining a bottom portion of the blade and a convex second surface defining a top portion of the blade; a connecting element extending from and/or coupled to the first end, wherein the connecting element is adjacent to the first surface; and a tip extending from and/or coupled to the second end.

In various other embodiments, a device is disclosed. The device may include a curved, substantially elongate blade, wherein a first curvature of the blade extends toward the second surface away from a central point along the transverse axis of the blade, the blade further including: a first surface defining a bottom portion of the blade; and a second surface defining a top portion of the blade a first end and a second end running along a longitudinal axis of the blade; a first edge and a second edge running along a transverse axis of the blade such that the first edge and the second edge define a width of the blade; and a second curvature running from the first edge to the second edge such that the first surface is concave and the second surface is convex; the second curvature may have a length defined by a maximum distance between the second surface and a plane defined by the first edge and the second edge at a given point along the longitudinal axis of the blade; and the width of the blade may be at least four times the length of the second curvature; a connecting element extending from and/or coupled to the first end, wherein the connecting element may be adjacent to the first surface; and a tip extending from and/or coupled to the second end.

In various embodiments, a device is disclosed. The device may include: a substantially elongate blade, the blade being substantially straight along its longitudinal axis and including: a first surface defining a bottom portion of the blade; and a second surface defining a top portion of the blade; a first end and a second end running along a longitudinal axis of the blade; a first edge and a second edge running along a transverse axis of the blade such that the first edge and the second edge define a width of the blade; and a first curvature running from the first edge to the second edge such that: the first surface is concave and the second surface is convex; the first curvature may have a length defined by a maximum distance between the second surface and a plane defined by the first edge and the second edge at a given point along the longitudinal axis of the blade; and the width of the blade may be at least four times the length of the first curvature; a connecting element extending from and/or coupled to the first end, wherein the connecting element is adjacent to the first surface; and a tip extending from and/or coupled to the second end, wherein the tip extends towards the first surface.

The laryngoscopes described herein may be formed of various materials. For instance the laryngoscopes may be formed of metal, such as steel, or one or more plastic materials. The laryngoscopes described herein may additionally include several other components. For instance, a camera may be included for recording the examination of a patient's throat. In some embodiments, the camera may be included with a light source disposed on a surface of the blade. In some embodiments, the camera may be connected to a connecting element. The connecting element may be used to connect to a handle for increased dexterity. The connecting element may additionally connect to a power source to provide power to the camera and/or light source.

DETAILED DESCRIPTION

The present disclosure, as set forth above, is generally directed to various embodiments of laryngoscopes that allow users to look into a person's throat and insert various other devices therein without excessively interacting with the person's teeth or other vital organs.

Figures 1, 2:
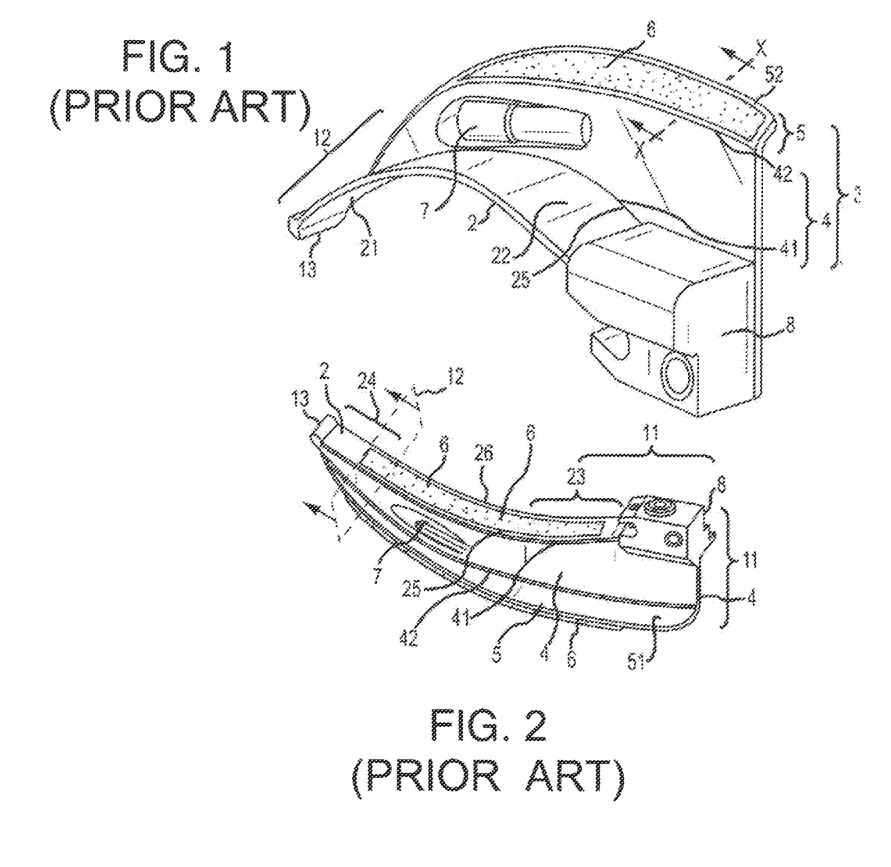
FIG. 1 and FIG. 2 are prior art laryngoscopes.

FIGS. 1 and 2 are prior art laryngoscopes, as originally shown in Pourshams. The laryngoscope of FIG. 1 is a typical curved laryngoscope that is well known and highly popular within the prior art. As shown in FIG. 1, the prior art laryngoscope discloses a flange that extends perpendicular to the longitudinal axis of the blade. Specifically, the blade itself has a first end and a second end extending along a transverse axis, and a relatively short width between the first end and the second end. As shown more clearly in FIG. 2, the flange extends from one end of the blade upward along a vertical axis, and then extends outward along the transverse axis.

As also shown by the exemplary embodiments of FIGS. 1 and 2, prior art laryngoscopes typically include a blade that is curved along the vertical axis, but not curved (rather, in fact, substantially straight) along the transverse axis. Accordingly, in order to control the tongue of a patient during intubation, the flange was necessary to move the tongue aside in order to visualize the patient's throat and access the larynx.

As stated above, however, it is difficult to control the tongue, and additionally difficult to move the patient's epiglottis, which is necessary to visualize the throat and larynx of many patients. As such, "rocking the blade" is often necessary, during which the teeth of the patient is used as a fulcrum that provides the necessary leverage to easily move the tongue and epiglottis of the patient, often causing substantial damage to the patient's teeth. Accordingly, a laryngoscope that utilizes a blade that lacks a flange as disclosed in the prior art is necessary to minimize the risk of direct contact between a laryngoscope blade and a patient's teeth, thereby minimizing damage to the patient's teeth, edentulous ridge, and other sensitive tissues in or around the patient's mouth.

Figure 3:
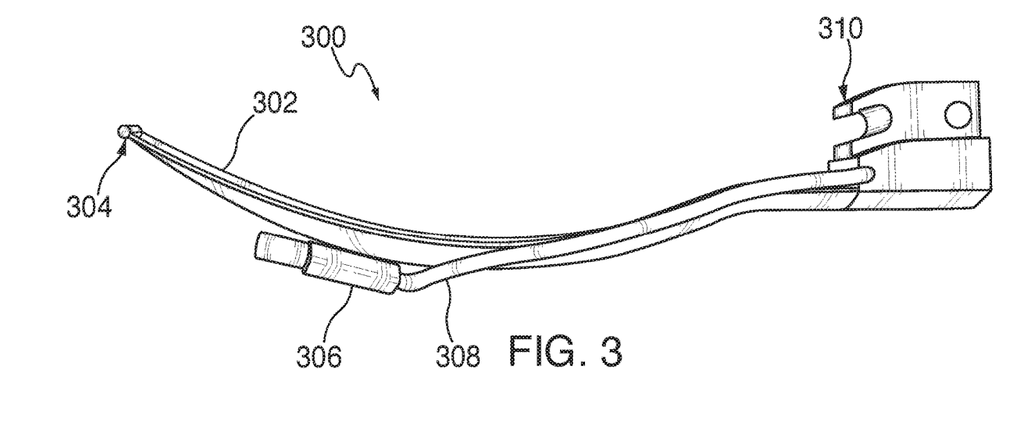
FIG. 3 is a side view of a laryngoscope, in accordance with various embodiments.

FIG. 3 is a side view of a laryngoscope, in accordance with various embodiments. As shown in FIG. 3 the laryngoscope 300 includes a curved, substantially elongate blade 302, a tip 304, a light source 306, a cable 308, and a connecting element 310. In some embodiments, blade 302 includes a first end and a second end. In some embodiments, blade 302 may be curved such that it forms a slight hook shape. This curvature may be ergonomic, allowing the laryngoscope to extend along the mouth of a patient and easily into the throat of the patient. As will be shown in greater detail below, blade 302 additionally includes a first end and a second end, and a curvature between the first end and the second end.

In some embodiments, laryngoscope 300 includes a tip 304 extending from blade 302. Tip 304 may be a short protrusion that acts to move a patient's epiglottis into proper position during examination and/or intubation. Tip 304 may be formed of the same material as the rest of the laryngoscope. As shown in FIG. 3, tip 304 follows along the same direction with the curvature of blade 302.

In some embodiments, laryngoscope 300 includes a light source 306 coupled via cable 308 to a connecting element 310. Light source 306 may be further coupled to, or otherwise secured to, blade 102 such that an operator is enabled to view the contents of a patient's mouth and/or throat during observation and intubation.

Cable 308 may be connected to a power source via connecting element 310. Accordingly, electricity may run from a power source electrically coupled to connecting element 310 through cable 308 into light source 306.

Connecting element 310 may be used to couple blade 302 to a handle for increased dexterity during examination and intubation. Additionally, connecting element may include a power source to be electrically coupled to light source and/or a camera, as described below.

In some embodiments, laryngoscope 300 may also include, in addition to or in the alternative to light source 306, a camera. The camera may be connected to the power source electrically coupled to connecting element 310, or may include its own power source. In some embodiments, however, the camera may be coupled to blade 302 of laryngoscope 300 on its own. In some embodiments, particularly where the laryngoscope is formed of a plastic material (e.g., the blade is formed of a plastic sheath), the camera may similarly be formed of a lightweight material that allows easier dexterity during examination and intubation.

Figure 4:
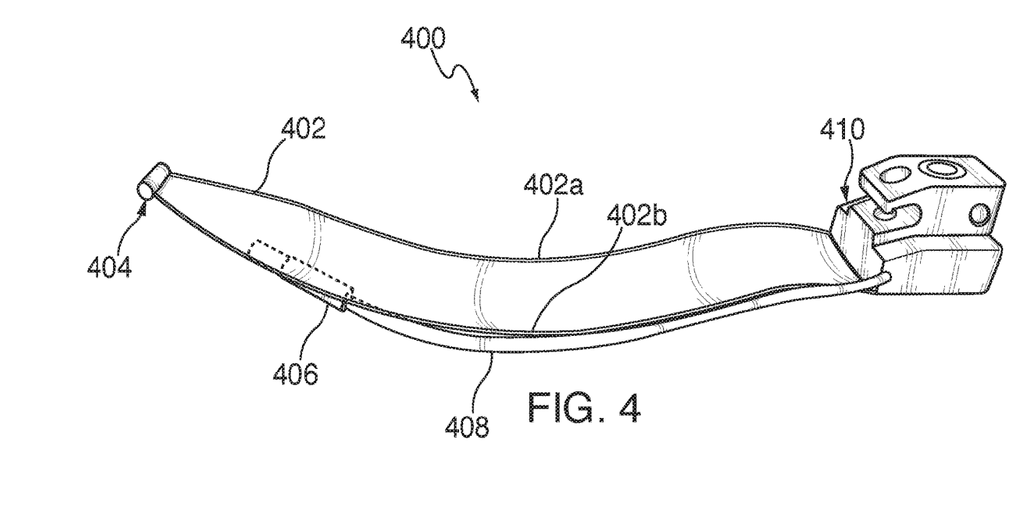
FIG. 4 is a perspective view of a laryngoscope, in accordance with various embodiments.

FIG. 4 is a perspective view of a laryngoscope, in accordance with various embodiments. As shown in FIG. 4 the laryngoscope 400 includes a curved, substantially elongate blade 402, a tip 404, a light source 406, a cable 408, and a connecting element 410. These structural features may be substantially identical to the features disclosed and described in FIG. 3. However, most notably shown in FIG. 4 that is not particularly evident in FIG. 3 is the fact that blade 402 may include a first surface defining a bottom portion of blade 402 and a second surface defining a top portion of blade 402. Blade 402 may additionally include a first edge 402a and a second edge 402b that extend along a transverse axis and thereby define a width of blade 402. In some embodiments, a curvature may be present between the first edge 402a and the second edge 402b such that the first surface is concave, and the second surface is convex.

By having a concave first surface, laryngoscope 400 is capable of curving around, and thereby controlling a patient's tongue upon the first surface coming into direct contact with the patient's tongue. Additionally, by having a curvature along its longitudinal axis, laryngoscope 400 is able to ergonomically fit through the patient's mouth and into the patient's throat for visualization and intubation.

Figure 5:
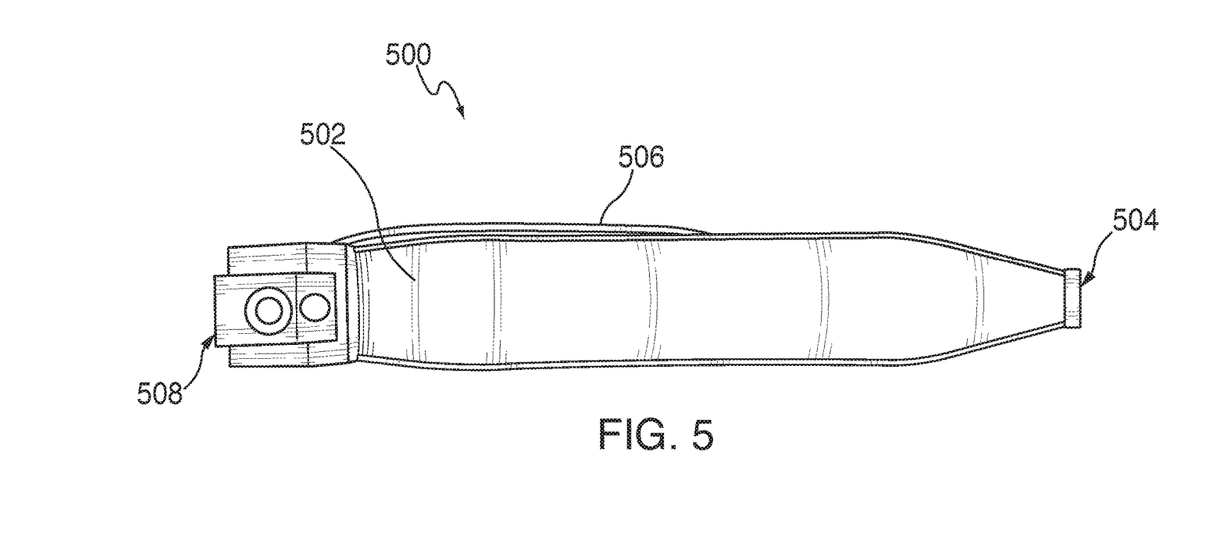
FIG. 5 is a bottom view of a laryngoscope, in accordance with various embodiments.

FIG. 5 is a bottom view of a laryngoscope, in accordance with various embodiments. As shown in FIG. 5, laryngoscope 500 includes blade 502, tip 504, cable 506, and connecting element 508. In FIG. 5, the convex second surface of blade 502 is not shown, while the concave first surface of blade 502 is shown. When in use, the first surface comes into contact with the patient's tongue in order to control its movement as blade 502 is moved deeper into the patient's mouth and into the throat, where tip 504 will move the patient's epiglottis for visualization of the throat and intubation.

As shown in FIG. 5, tip 504 has a narrower width than the majority of blade 502. Accordingly, blade 502 narrows along its longitudinal axis as it extends toward tip 504. The narrowing of blade 502 at this end allows for a medical practitioner operating laryngoscope 500 to more easily enter the patient's throat, which has a much narrower opening than the patient's mouth. Additionally, the epiglottis is relatively small, and manipulation of the epiglottis is aided by the relatively finer tip 504, which further includes a small beak that essentially "hooks" the epiglottis and aides the practitioner in moving it downward as blade 502 is moved further into the patient's throat.

Connecting element 508 is located adjacent to the first surface of blade 502, rather than the second surface. As a handle is attached to connecting element 508 from the bottom of laryngoscope 500, a practitioner is provided with leverage and dexterity to place the downward force necessary to move the patient's epiglottis. However, as will be described below, the relatively short height of blade 502 along its vertical axis helps to prevent any contact between the patient's teeth and blade 502, thereby reducing the risk of injury to the patient's teeth.

Figure 6:
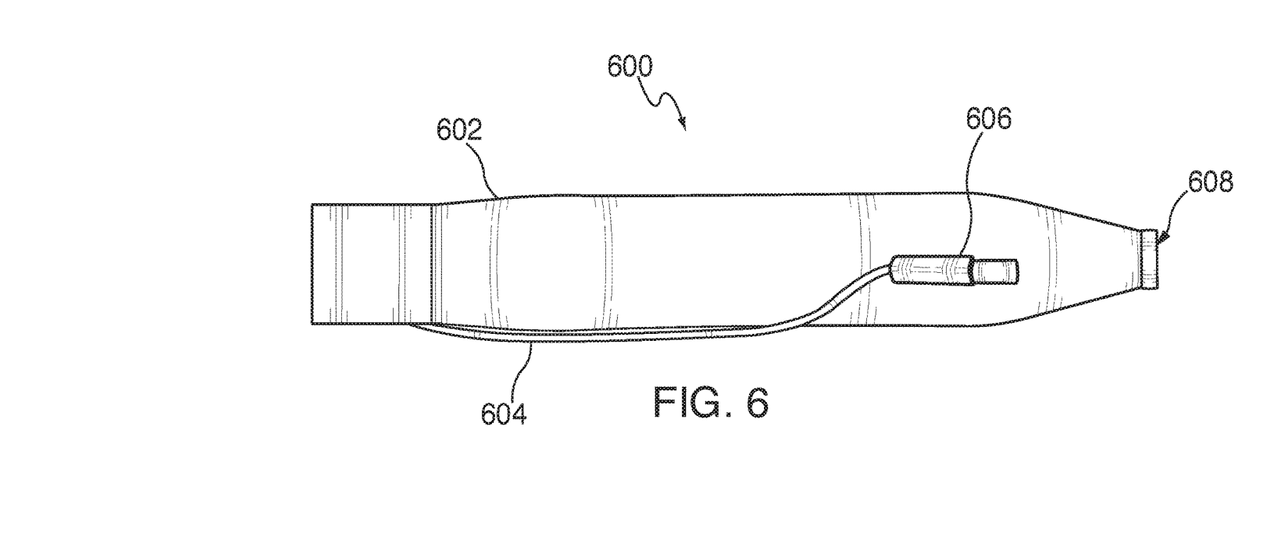
FIG. 6 is a top view of a laryngoscope, in accordance with various embodiments.

FIG. 6 is a top view of a laryngoscope, in accordance with various embodiments. Laryngoscope 600 includes blade 602, cable 604, light source 606, and tip 608. In FIG. 6, the first surface (i.e., the top portion) of blade 602 is shown. As shown in FIG. 6, the second surface is convex and smooth, lacking any indentations, protrusions, or flanges that would extend the vertical length of blade 602 or otherwise increase the risk of coming into direct contact with and/or damaging a patient's teeth.

Figure 7:
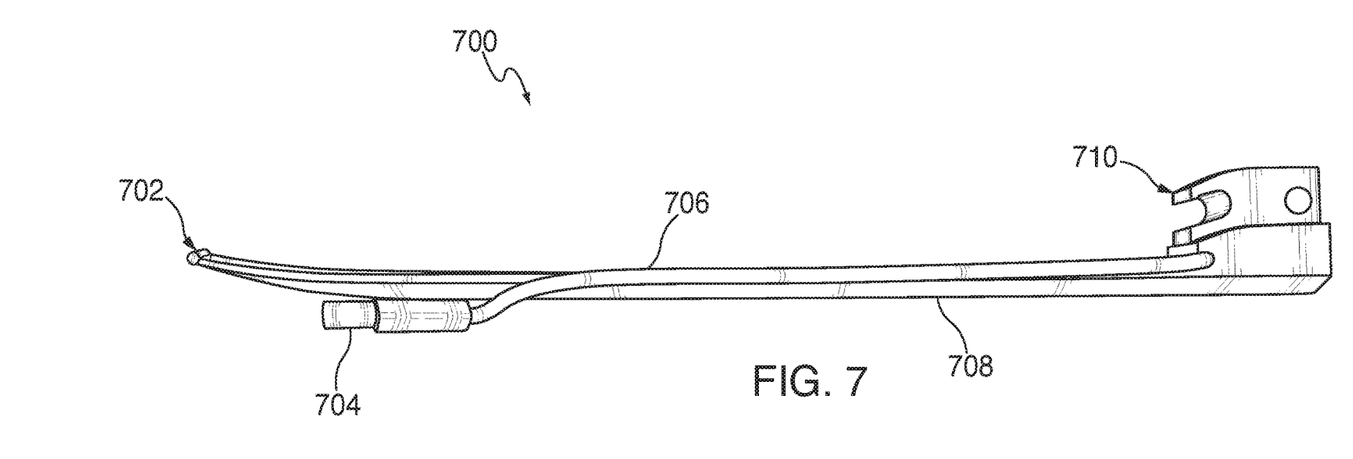
FIG. 7 is a side view of a laryngoscope, in accordance with various embodiments.

FIG. 7 is a side view of a straight laryngoscope, in accordance with various embodiments. As shown in FIG. 7, laryngoscope 700 includes a blade 708, which includes a tip 702 at a first end of blade 708, as well as a connecting element 710 at a second end of blade 708. Laryngoscope further includes a light source 704 and a cable 706. In contrast to the curved blades shown in FIGS. 3-6, blade 708 lacks a curvature along its central portion between its first and second ends. However, blade 708 extends slightly downward at tip 702, which aides in the manipulation of the epiglottis.

Figure 8:
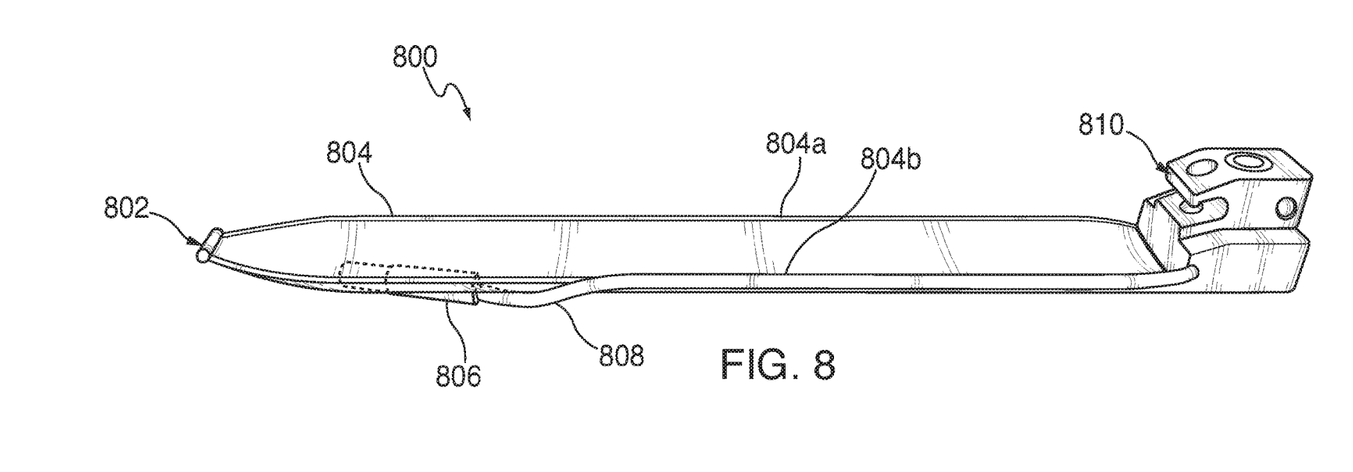
FIG. 8 is a perspective view of a laryngoscope, in accordance with various embodiments.

FIG. 8 is a perspective view of a straight laryngoscope, in accordance with various embodiments. Laryngoscope 800 includes a tip 802, a blade 804, a light source 806, a cable 808, and a connecting element 810. Similar to the curved blades of FIGS. 3-6, blade 804 includes a first surface defining a bottom portion of blade 804, a second surface defining a top portion of blade 804, first edge 804a, and a second edge 804b that extend along a transverse axis of blade 804 and define a width of blade 804. As will be described in greater detail below, a curvature exists between first edge 804a and second edge 804b such that the first surface is concave, while the second surface is convex, allowing the first surface to control a patient's tongue upon contact during examination and/or intubation.

Figure 9:
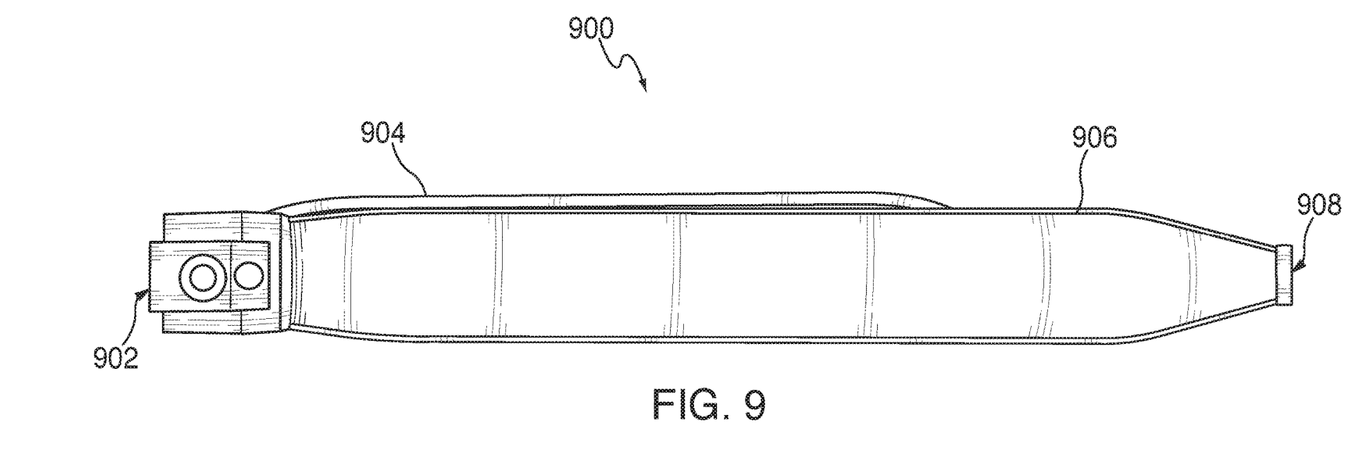
FIG. 9 is a bottom view of a laryngoscope, in accordance with various embodiments.

FIG. 9 is a bottom view of a laryngoscope, in accordance with various embodiments. As shown in FIG. 9, laryngoscope 900 includes blade 906, tip 908, cable 904, and connecting element 902. In FIG. 9, the convex second surface of blade 906 is not shown, while the concave first surface of blade 906 is shown. When in use, the first surface comes into contact with the patient's tongue in order to control its movement as blade 906 is moved deeper into the patient's mouth and into the throat, where tip 908 will move the patient's epiglottis for visualization of the throat and intubation.

As shown in FIG. 9, tip 908 has a narrower width than the majority of blade 906. Accordingly, blade 906 narrows along its longitudinal axis as it extends toward tip 908. The narrowing of blade 906 at this end allows for a medical practitioner operating laryngoscope 900 to more easily enter the patient's throat, which has a much narrower opening than the patient's mouth. Additionally, the epiglottis is relatively small, and manipulation of the epiglottis is aided by the relatively finer tip 908, which further includes a small beak that essentially "hooks" the epiglottis and aides the practitioner in moving it downward as blade 906 is moved further into the patient's throat.

Connecting element 902 is located adjacent to the first surface of blade 906, rather than the second surface. As a handle is attached to connecting element 902 from the bottom of laryngoscope 900, a practitioner is provided with leverage and dexterity to place the downward force necessary to move the patient's epiglottis. However, as will be described below, the relatively short height of blade 906 along its vertical axis helps to prevent any contact between the patient's teeth and blade 906, thereby reducing the risk of injury to the patient's teeth.

Figure 10:
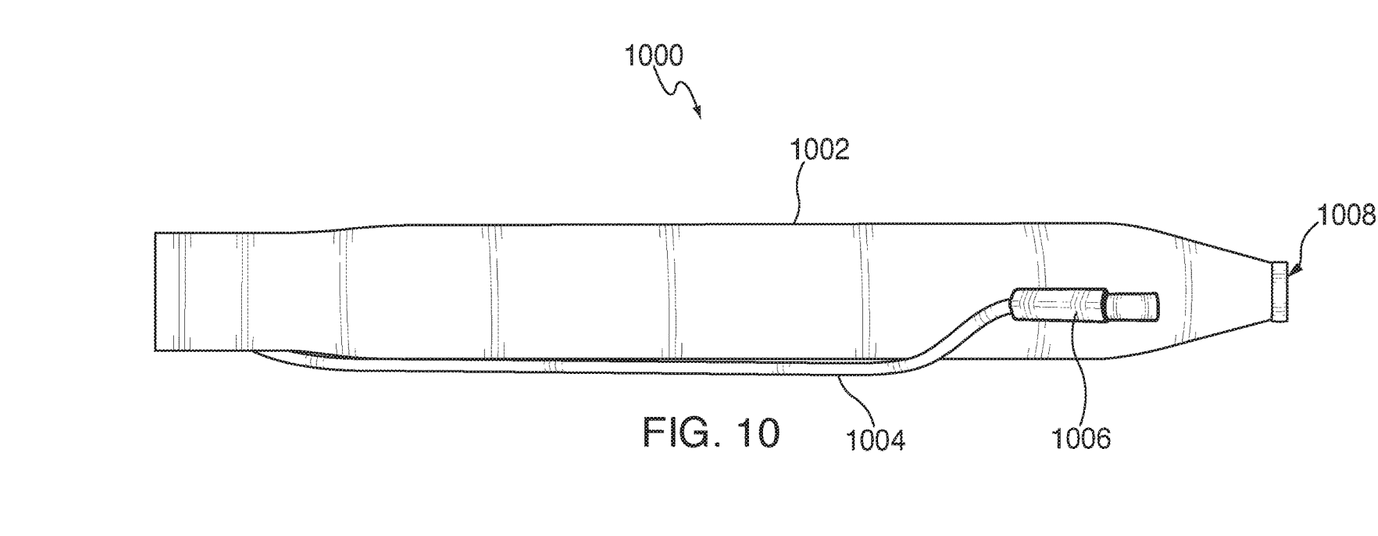
FIG. 10 is a top view of a laryngoscope, in accordance with various embodiments.

FIG. 10 is a top view of a laryngoscope, in accordance with various embodiments. Laryngoscope 1000 includes blade 1002, tip 1008, cable 1004, and light source 1006. In FIG. 10, the first surface (i.e., the top portion) of blade 1002 is shown. As shown in FIG. 10, the second surface is convex and smooth, lacking any indentations, protrusions, or flanges that would extend the vertical length of blade 1002 or otherwise increase the risk of coming into direct contact with and/or damaging a patient's teeth.

Figure 11:
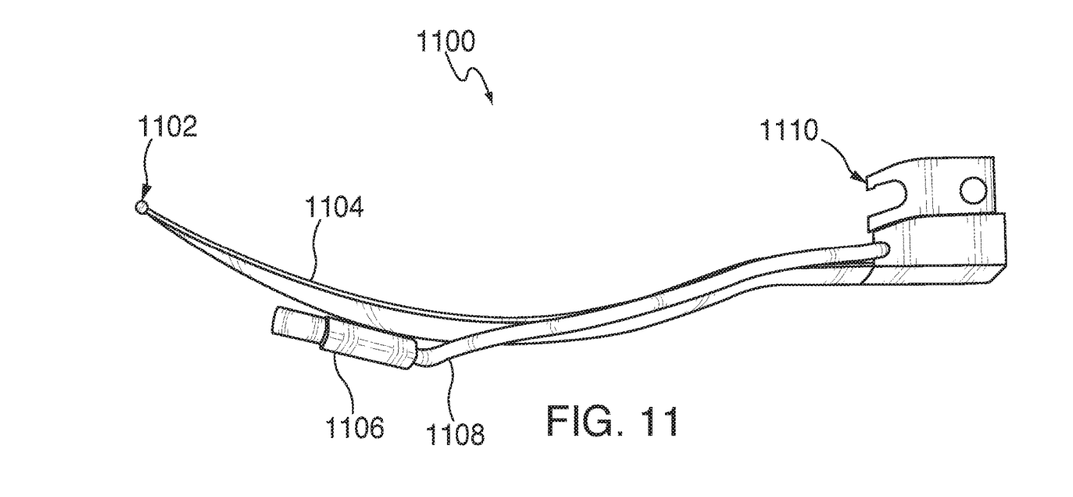
FIG. 11 and FIG. 12 are side views illustrating a side-by-side comparison of a curved laryngoscope and a straight laryngoscope, in accordance with various embodiments.
Figure 12:
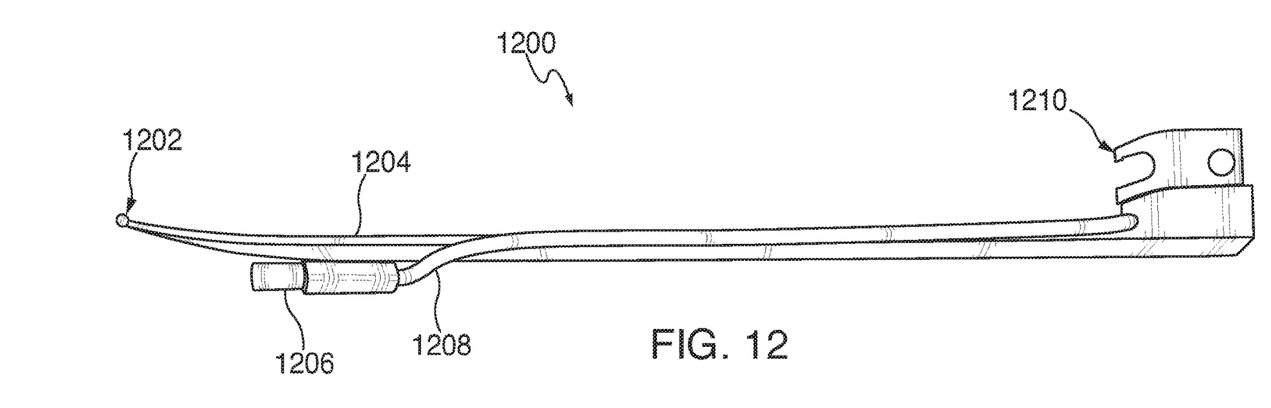

FIGS. 11 and 12 are side-by-side comparisons of a curved laryngoscope and a straight laryngoscope, in accordance with various embodiments. As is evident in FIGS. 11 and 12, laryngoscope 1100 and laryngoscope 1200 are very similar, with at least one important difference. Specifically, tips 1102 and 1202, light sources 1106 and 1206, cables 1108 and 1208, and connecting elements 1110 and 1210 are substantially identical. However, blade 1104 includes a curvature along its longitudinal axis such that it forms a slight hook shape from a side view, whereas blade 1204 lacks such a curvature. As such, tip 1102 largely follows the direction of the curvature as it points downward (i.e., toward the ventral surface). In contrast, while there is no curvature along the longitudinal axis of blade 1204, tip 1202 extends downward (i.e., toward the ventral surface), rather than continue straight outward along the longitudinal axis of blade 1204. However, as will be shown in FIG. 13, both are capable of controlling a patient's tongue during examination and intubation due to the substantially identical curvatures of blades 1104 and 1204 along their transverse axes.

Figure 13:
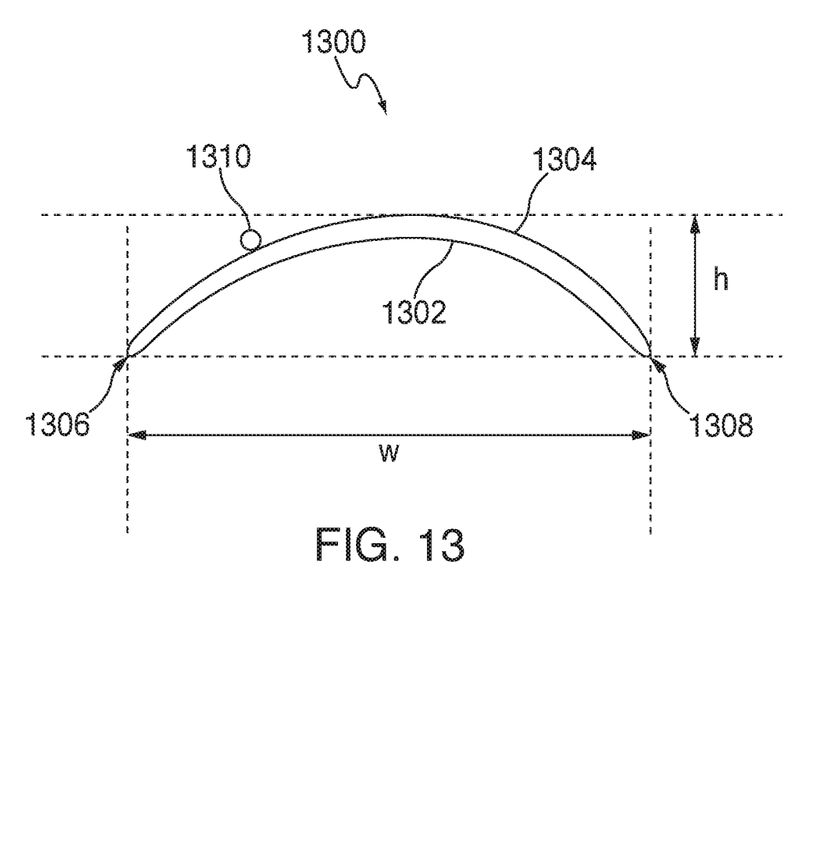
FIG. 13 is a cross-sectional view of a laryngoscope blade, in accordance with various embodiments.

FIG. 13 is a cross-sectional view of a laryngoscope blade, in accordance with various embodiments. The blade shown in FIG. 13 may be a blade of a curved (e.g., FIGS. 3-6 and 11) or straight laryngoscope (e.g., FIGS. 7-10 and 12), as both laryngoscopes include a curvature along their transverse axes. Blade 1300 includes a first surface 1302 defining a bottom portion of blade 1300, a second surface 1304 defining a top portion of laryngoscope 1300, a first edge 1306 and a second edge 1308 extending along the cross-section (i.e., the transverse axis), and a light source 1310 affixed to second surface 1304.

First edge 1306 and second edge 1308 include a curvature between them such that first surface 1302 is concave and second surface 1304 is convex. The curvature is such that at any point along the longitudinal axis of blade 1300, a height h (i.e., length along a vertical axis) of blade 1300 may be defined by the greatest distance between second surface 1304 and a plain along the transverse axis that is defined by first edge 1306 and second edge 1308. In addition, the distance between first edge 1306 and second edge 1308 along the transverse axis define a width w of blade 1300. While FIG. 13 is not drawn to scale, the dimensions of blade 1300 may be such that the length of width w could be at least four times the length of height h.

Although the above-described embodiments of the present invention are described herein in some detail via illustration and example for purposes of clarity and understanding, it will be apparent to those skilled in the art that certain changes and modifications may be practiced within the spirit and scope of the present invention. Therefore, the subject matter described herein the appended claims is not necessarily limited to the specific features and embodiments described herein.

What is claimed is:

1. A device, comprising:
   a substantially elongate blade, comprising:
     a first end and a second end running along a longitudinal axis of the blade, wherein the blade runs, from the first end to the second end, straight and parallel to the longitudinal axis;
     a first edge and a second edge running along a transverse axis of the blade such that the first edge and the second edge define a width of the blade;
     a first curvature running from the first edge to the second edge such that the blade further comprises:
       a concave first surface defining a bottom portion of the blade; and
       a convex second surface defining a top portion of the blade;
     a connecting element at least one of extending from and coupled to the first end, wherein the connecting element is adjacent to the first surface, the connecting element structured to be connected to a camera or a power source for the camera; and
     a tip at least one of extending from and coupled to the second end, the tip comprising a beak structured to move an epiglottis of a patient into a proper position for examination, wherein the blade lacks a flange extending perpendicular to the longitudinal axis of the blade which is otherwise structured to control the tongue of the patient during the examination.

2. The device of claim 1, wherein the blade further comprises a second curvature running from the first end to the second end.

3. The device of claim 2, further comprising a light source coupled to the blade and disposed along the second surface.

4. The device of claim 3, wherein the light source is further coupled to the connecting element.

5. The device of claim 2, wherein the second curvature of the blade extends toward the second surface approximately 25 millimeters away from a central point along the transverse axis of the blade.

6. The device of claim 5, wherein the width of the blade is approximately 25 millimeters.

7. The device of claim 2, wherein the first curvature has a length defined by a maximum distance between the second surface and a plane defined by the first edge and the second edge at a given point along the longitudinal axis of the blade, and wherein the width of the blade is at least four times the length of the first curvature.

8. The device of claim 1, wherein the first curvature has a length defined by a maximum distance between the second surface and a plane defined by the first edge and the second edge at a given point along the longitudinal axis of the blade, and wherein the width of the blade is at least four times the length of the first curvature.

9. A device, comprising:
   a curved, substantially elongate blade, wherein a first curvature of the blade extends toward a second surface away from a central point along a transverse axis of the blade, the blade further comprising:
     a first surface defining a bottom portion of the blade; and
     the second surface defining a top portion of the blade;
     a first end and a second end running along a longitudinal axis of the blade, wherein the blade runs, from the first end to the second end, straight and parallel to the longitudinal axis;

a first edge and a second edge running along a transverse axis of the blade such that the first edge and the second edge define a width of the blade; and a second curvature running from the first edge to the second edge such that:

the first surface is concave and the second surface is convex;

the second curvature has a length defined by a maximum distance between the second surface and a plane along the transverse axis that is defined by the first edge and the second edge at a given point along the longitudinal axis of the blade; and the width of the blade is at least four times the length of the second curvature;

a connecting element at least one of extending from and coupled to the first end, wherein the connecting element is adjacent to the first surface, the connecting element structured to be connected to a camera or a power source for the camera; and a tip at least one of extending from and coupled to the second end, the tip comprising a beak structured to move an epiglottis of a patient into a proper position for examination, wherein the blade lacks a flange extending perpendicular to the longitudinal axis of the blade which is otherwise structured to control the tongue of the patient during the examination.

10. The device of claim 9, further comprising a light source coupled to the blade and disposed along the second surface.

11. The device of claim 10, wherein the light source is further coupled to the connecting element.

12. The device of claim 9, wherein the first curvature of the blade extends toward the second surface approximately 25 millimeters away from a central point along the transverse axis of the blade.

13. The device of claim 12, wherein the width of the blade is approximately 25 millimeters.

14. A device, comprising:

a substantially elongate blade, the blade being substantially straight along its longitudinal axis, comprising:

a first surface defining a bottom portion of the blade; and a second surface defining a top portion of the blade;

a first end and a second end running along a longitudinal axis of the blade, wherein the blade runs, from the first end to the second end, straight and parallel to the longitudinal axis;

a first edge and a second edge running along a transverse axis of the blade such that the first edge and the second edge define a width of the blade; and a first curvature running from the first edge to the second edge such that:

the first surface is concave and the second surface is convex;

the first curvature has a length defined by a maximum distance between the second surface and a plane along the transverse axis that is defined by the first edge and the second edge at a given point along the longitudinal axis of the blade; and the width of the blade is at least four times the length of the first curvature;

a connecting element at least one of extending from and coupled to the first end, wherein the connecting element is adjacent to the first surface, the connecting element structured to be connected to a camera or a power source for the camera; and a tip at least one of extending from and coupled to the second end, wherein the tip extends towards the first surface and comprises a beak structured to move an epiglottis of a patient into a proper position for examination, wherein the blade lacks a flange extending perpendicular to the longitudinal axis of the blade which is otherwise structured to control the tongue of the patient during the examination.

15. The device of claim 14, further comprising a light source coupled to the blade and disposed along the second surface.

16. The device of claim 14, wherein the first curvature of the blade extends toward the second surface approximately 25 millimeters away from a central point along the transverse axis of the blade.

17. The device of claim 16, wherein a width of the blade is approximately 25 millimeters.

* * * * *